United States Patent [19]

Zook

[11] Patent Number: 5,167,649

[45] Date of Patent: Dec. 1, 1992

[54] DRUG DELIVERY SYSTEM FOR THE REMOVAL OF DERMAL LESIONS

[76] Inventor: Gerald P. Zook, 9708 Woodlawn Ave. N., Seattle, Wash. 98103

[21] Appl. No.: 870,544

[22] Filed: Apr. 17, 1992

Related U.S. Application Data

[63] Continuation-in-part of Ser. No. 395,186, Aug. 18, 1989, abandoned, which is a continuation-in-part of Ser. No. 234,585, Aug. 22, 1988, abandoned.

[51] Int. Cl.$^5$ ............................................. A61F 13/02
[52] U.S. Cl. ................................. 604/307; 604/304; 602/48; 424/445; 424/447
[58] Field of Search ................ 602/48, 51; 604/304, 604/307, 308, 289; 424/445, 446, 447

[56] References Cited

U.S. PATENT DOCUMENTS

| | | | |
|---|---|---|---|
| 3,419,006 | 12/1968 | King | 602/48 |
| 4,158,359 | 6/1979 | Kurokawa et al. | 128/630 |
| 4,842,931 | 6/1989 | Zook | 428/354 |
| 4,988,341 | 1/1991 | Columbus et al. | 604/304 |
| 4,991,574 | 2/1991 | Pocknell | 602/48 |
| 5,098,421 | 3/1992 | Zook | 604/307 |
| 5,106,629 | 4/1992 | Cartmell et al. | 602/48 |
| 5,108,710 | 4/1992 | Little et al. | 604/307 |

Primary Examiner—Paul Prebilic
Attorney, Agent, or Firm—John F. Ingman

[57] ABSTRACT

A drug delivery system for the removal of dermal lesions which includes a pad of viscoelastic rubber and oil gel, perfused with a pharmacologically active substance, which is partially encapsulated between a first layer of oil and water impermeable material and a second layer of oil and water impermeable material. The second layer includes an aperture, corresponding to the dimension of the dermal lesion, which is smaller than, and located within, the periphery of the adjacent medicated viscoelastic rubber and oil gel pad. The two layers of oil and water impermeable material are bonded together to form a seal about the periphery of the viscoelastic rubber and oil gel pad. The surface of the patch which is affixed to a wearer's skin is provided with a pressure sensitive adhesive. The viscoelastic rubber and oil pad and the encapsulating layers preferably are transparent.

6 Claims, 1 Drawing Sheet

DRUG DELIVERY SYSTEM FOR THE REMOVAL OF DERMAL LESIONS

This is a continuation-in-part of co-pending application Ser. No. 07/395,186, filed Aug. 18, 1989 now abandoned which in turn is a continuation-in-part of Ser. No. 07/234,585, filed Aug. 22, 1988, now abandoned.

BACKGROUND OF THE INVENTION

1. Field of the Invention

This invention relates to the field of drug delivery systems for the topical administration of medication, and, in particular, to a device incorporating a viscoelastic rubber and oil gel for the removal of dermal lesions such as warts, actinic keratoses, superficial tumors, and the like.

2. Description of the Prior Art

Historically, most drug delivery systems for the topical treatment of dermal lesions have consisted of solutions, tinctures, creams, ointments, and the like, which are applied in an unprotected manner to the dermal lesion being treated. Such unprotected vehicles may be rubbed off by clothing, including socks. For example, most over-the-counter wart removal products consist of an active agent dissolved in a flexible collodion vehicle which dries to leave a film of acid on the wart. These products have the disadvantage of requiring a substantial time for a volatile solvent to evaporate. Furthermore, such products dissolve normal tissue unless applied only to the wart. Such products often are rubbed off by socks when applied to the plantar aspect of the foot or are washed off with bathing.

SUMMARY OF THE INVENTION

Accordingly, it is an object of the present invention to provide a drug delivery system for dermal lesions that is easy to apply by utilizing a transparent patch with an aperture corresponding to the dimension of the dermal lesion being treated.

It is a further object of the present invention to provide a drug delivery system for dermal lesions which is protective of the lesion while in use.

It is a further object of the present invention to provide a drug delivery system which is waterproof and can be worn while bathing.

Yet another object of the present invention is to provide a drug delivery system which can be peeled off the skin and discarded at will.

The present invention is a "patch" type of drug delivery system comprising a viscoelastic rubber and oil gel perfused with a pharmacologically active substance and partially encapsulated by an oil and water impermeable transparent bandage which allows direct contact by the medication only upon the dermal lesion being treated. The rubber component is preferably a triblock copolymer of styrene-ethylene-butylene-styrene, and the oil fraction is preferably Mineral Oil, U.S.P. Desirable pharmacologically-active agents include, but are not limited to, cantharidin, podophyllin, salicylic acid, lactic acid, trichloracetic acid, and 5-fluorouracil.

The preferred embodiment of the drug delivery system for the removal of dermal lesions includes a pad of viscoelastic rubber and oil gel which is partially encapsulated between a first layer of oil and water impermeable material and a second layer of oil and water impermeable material. The second layer includes an aperture which is smaller than, and located within, the periphery of the adjacent viscoelastic rubber and oil gel pad. The two layers of oil and water impermeable material are bonded together to form a seal about the periphery of the viscoelastic rubber and oil gel pad. The surface of the patch which is affixed to a wearer's skin is provided with a pressure sensitive adhesive.

DETAILED DESCRIPTION OF THE INVENTION

Figure 1:
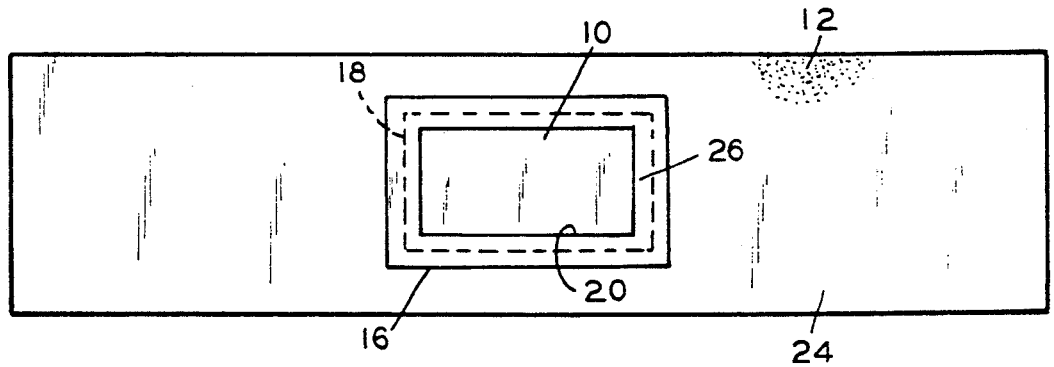
FIG. 1 is a plan view of a preferred embodiment of the drug delivery system for the removal of dermal lesions.

Applicant conceived of this invention while making gel bandages as described in U.S. Pat. No. 4,842,931. As a podiatrist, applicant had treated numerous patients with a vesicant/keratolytic compound known as VERRUSOL (C&M Pharmacal). This agent kills warts by causing acantholysis and blister formation to occur under the wart which separates the wart from its blood supply and results in death of the wart (see Treatment of Plantar Warts in Children with a Salicylic Acid-Podophyllin-Cantharidin Product, Pediatric Dermatology, Vol. 2, No. 1, 71-73, Jul. 1984). The problem with VERRUSOL is that it is technically difficult to use. The skin around the wart must be protected from the VERRUSOL which involves a cumbersome and time-consuming procedure such as applying tincture of benzoin to the skin around the wart or fashioning a piece of adhesive tape, adhesive felt, or the like, such that it has an aperture of just the right size to fit around the wart, so that the wart is exposed but the adjacent normal skin is protected. Next, the VERRUSOL is applied to the wart and then sufficient time must be allowed to permit the solvent to evaporate, leaving a crumbly, crusty layer of VERRUSOL on the wart. Following this, an occlusive layer, such as plastic tape, is applied to improve penetration of the VERRUSOL. The patient then is instructed to keep the foot dry for 24-48 hours and return to the office for removal of the dressing and medication. With this in mind, applicant decided to incorporate one or more of the active ingredients in VERRUSOL (i.e., cantharidin, podophyllin, salicylic acid, and the penetration enhancer octylphenyl-polyethylene glycol) into a viscoelastic rubber and oil gel such as the type described by Shell Technical Bulletin SC:1102-89, and, in turn, to incorporate this medication loaded gel into a patch that could be affixed to the patient's skin by means of a pressure sensitive adhesive. Use of the viscoelastic rubber and oil gel also provided a cushioning, protective pad, which is of particular importance when the patch is applied to the foot within a shoe. One problem with this concept was devising a means to prevent the viscoelastic rubber and oil gel from flattening out or increasing its surface area of contact beyond the borders of the dermal lesion such that the medication could contact normal skin and cause damage to it.

A solution to the problem is the incorporation of the medicated viscoelastic rubber and oil gel into a patch which encapsulates the gel with the exception of an aperture or window. This patch would have a first layer of material which is impermeable to oil, the liquid fraction of the gel, which completely covers one surface of the gel and a second layer of oil impermeable material covering the opposite surface of the gel with the exception of an aperture or window through which the medicated viscoelastic rubber and oil gel would directly contact the wart. This patch would be affixed by means of pressure sensitive adhesive upon the side of the patch in which the aperture is formed. The two layers of oil-impermeable material would be joined, adjacent to the periphery of the medicated viscoelastic rubber and oil gel, to form a seal and prevent migration of the gel. The two layers encapsulating the medicated viscoelastic rubber and oil gel also would be impermeable to water to permit the patient to bathe during the period that the patch is applied. At the end of the period of application the patch is easily peeled off of the skin and discarded.

Figure 2:
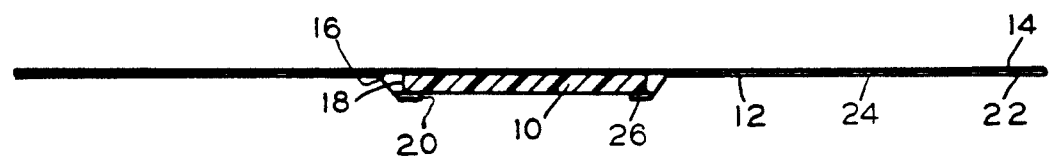
FIG. 2 is a cross-sectional side view of the drug delivery system of FIG. 1.

Turning now to the drawings, in order to facilitate a better understanding of the invention, there is shown in FIGS. 1 and 2 a preferred embodiment of the drug delivery system for the removal of dermal lesions. A pad 10 of viscoelastic rubber and oil gel is partially encapsulated between a first layer 14 of oil and water impermeable material and a second layer 22 of oil and water impermeable material. The second layer 22 includes an aperture 20 which is smaller than, and located within, the periphery 18 of the adjacent viscoelastic rubber and oil gel pad 10. The aperture 20 is formed to correspond to the size of the dermal lesion being treated. The two layers of oil and water impermeable material, 14 and 22, are bonded together to form seal 16 about the periphery 18 of the viscoelastic rubber and oil gel pad 10. The surface 24 of the patch which is affixed to the wearer's skin, the second oil and water impermeable layer 22 as illustrated in the preferred embodiment, is provided with a pressure sensitive adhesive 12.

The viscoelastic rubber and oil gel pad 10 preferably is formed of one of the thermoplastic compositions sold by Shell Oil (Houston, Tex.) under the name KRATON and described in Shell Technical Bulletin SC:1102-89, comprising a styrene-ethylene-butylene-styrene triblock copolymer rubber and oil gel. Preferably the plasticizing oil is Mineral Oil, U.S.P. The margin 26 of layer 22 defines the aperture 20 which allows the gel pad 10 to come into direct contact with, and only with, the dermal lesion being treated. The bond and seal 16 between the layers 14, 22 may be created by a thermal weld, or alternatively accomplished by an adhesive. Preferably both the viscoelastic rubber and oil gel pad 10 and the layers 14 and 22 of oil and water impermeable material are transparent, so as to allow precise application of the aperture 20 upon the dermal lesion and to allow subsequent medical viewing of the condition of the dermal lesion without removal. The oil and water impermeable encapulating layers 14 and 22 may be a transparent impermeable plastic tape with layer 22, wherein the aperture 20 is formed, being provided on its surface 24 with a pressure sensitive adhesive 12.

Medication utilized in conjunction with the drug delivery system for the removal of dermal lesions may include cantharidin, podophyllin, salicylic acid, lactic acid, trichloracetic acid, and 5-fluorouracil.

Figure 3:
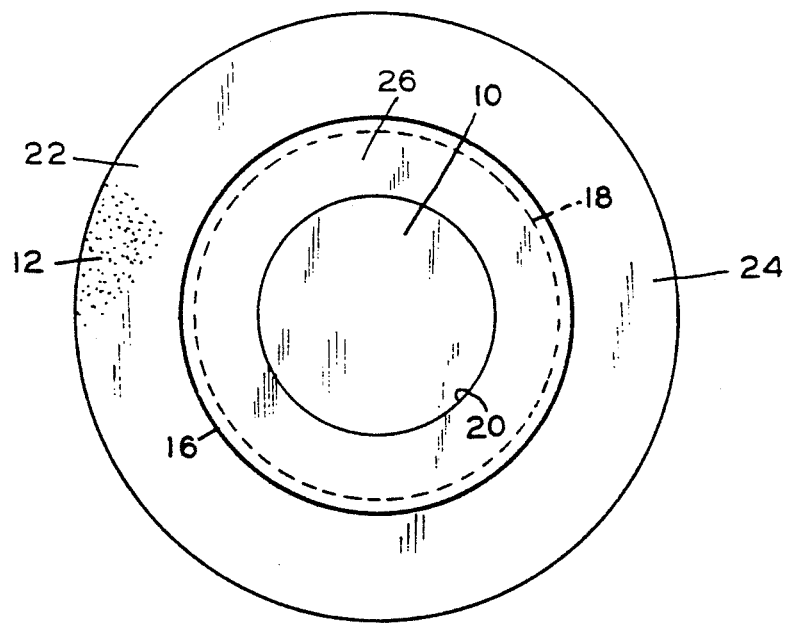
FIG. 3 is a plan view of an alternative shape of the drug delivery system for the removal of dermal lesions.

The viscoelastic rubber and oil gel pad 10 may be rectangular as illustrated in FIGS. 1 and 2, circular as illustrated in FIG. 3, or any shape which would facilitate its function as a padding and as a drug dispensing system. The viscoelastic rubber and oil gel pad 10 preferably is approximately 1.0 mm to 5.0 mm thick to be effective as a cushioning and medicating device.

It is thought that the drug delivery system for the removal of dermal lesions of the present invention and its many attendant advantages will be understood from the foregoing description and that it will be apparent that various changes in form, construction and arrangement of the parts thereof may be made without departing from the spirit and scope of the invention or sacrificing all of its material advantages, the form hereinbefore described being merely an exemplary embodiment thereof.

I claim:

1. A drug delivery system, in the form of a patch, having a surface affixed to a wearer's skin, for the removal of dermal lesions, comprising:
   a. a viscoelastic rubber and oil gel pad, having a first surface, an opposing second surface, and a periphery, said viscoelastic rubber and oil gel pad being perfused with a pharmacologically active substance;
   b. a first layer of oil and water impermeable material, covering said first surface of said viscoelastic rubber and oil gel pad; and
   c. a second layer of oil and water impermeable material, having an aperture formed therein of less dimension than said second surface of said viscoelastic rubber and oil gel pad; said second layer of oil and water impermeable material, except for said aperture, covering said second surface of said viscoelastic rubber and oil gel pad; said aperture being positioned upon said second surface, and within said periphery, of said viscoelastic rubber and oil gel pad;
   d. said first and second layers of oil and water impermeable material being joined to form a seal about the periphery of said viscoelasic rubber and oil gel pad, so as to encapsulate said viscoelastic rubber and oil gel pad except for said aperture;
   e. wherein a portion of said second surface of said viscoelastic rubber and cil gel pad is exposed through said aperture and is held in direct contact with a dermal lesion when said patch is applied to a wearer's skin.

2. The drug delivery system for the removal of dermal lesions, as recited in claim 1, wherein said first and second layers of oil and water impermeable material and said viscoelastic rubber and oil gel pad all are substantially transparent.

3. The drug delivery system for the removal of dermal lesions, as recited in claim 1, wherein said pharmacologically active substance includes one or more agents from the following group: cantharidin, podophyllin, salicylic acid, lactic acid, trichloracetic acid, and 5-fluorouracil.

4. The drug delivery system for the removal of dermal lesions, as recited in claim 1, wherein the rubber of said viscoelastic rubber and oil gel is a triblock copolymer of styrene-ethylene-butylene-styrene.

5. The drug delivery system for the removal of dermal lesions, as recited in claim 1, wherein the oil of said viscoelastic rubber and oil gel is Mineral Oil, U.S.P.

6. The drug delivery system for the removal of dermal lesions, as recited in claim 1, wherein, additionally, a means of affixing the surface of the patch to the wearer's skin includes pressure sensitive adhesive.

* * * * *